(12) United States Patent
Rapoport

(10) Patent No.: US 9,182,461 B2
(45) Date of Patent: *Nov. 10, 2015

(54) HIGH RESOLUTION HIGH CONTRAST MRI FOR FLOWING MEDIA

(71) Applicant: ASPECT IMAGING LTD., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 516 days.

This patent is subject to a terminal disclaimer.

(21) Appl. No.: 13/652,780

(22) Filed: Oct. 16, 2012

(65) Prior Publication Data

US 2013/0328559 A1 Dec. 12, 2013

Related U.S. Application Data

(60) Provisional application No. 61/656,041, filed on Jun. 6, 2012, provisional application No. 61/661,897, filed on Jun. 20, 2012.

(51) Int. Cl.
*G01V 3/00* (2006.01)
*G01R 33/32* (2006.01)
*G01R 33/44* (2006.01)
*G01R 33/56* (2006.01)
*G01N 24/08* (2006.01)

(52) U.S. Cl.
CPC .............. *G01R 33/32* (2013.01); *G01R 33/445* (2013.01); *G01R 33/56* (2013.01); *G01N 24/084* (2013.01)

(58) Field of Classification Search
CPC ....................................................... G01R 33/32
USPC ........................................................... 324/309
See application file for complete search history.

(56) References Cited

U.S. PATENT DOCUMENTS

| 4,697,594 | A | * | 10/1987 | Mayo, Jr. ...................... 600/443 |
| 5,168,226 | A | | 12/1992 | Hinks |
| 5,208,534 | A | * | 5/1993 | Okamoto et al. ............. 324/309 |
| 5,479,925 | A | | 1/1996 | Dumoulin et al. |
| 8,807,084 | B2 | | 8/2014 | Rapoport et al. |
| 8,851,018 | B2 | | 10/2014 | Rapoport et al. |
| 8,896,310 | B2 | | 11/2014 | Rapoport |
| 2004/0169512 | A1 | | 9/2004 | Jara |
| 2005/0203420 | A1 | * | 9/2005 | Kleen et al. ................... 600/476 |
| 2010/0133488 | A1 | * | 6/2010 | Giakos ......................... 252/582 |
| 2011/0162652 | A1 | | 7/2011 | Rapoport |
| 2011/0186049 | A1 | | 8/2011 | Rapoport |
| 2011/0234347 | A1 | | 9/2011 | Rapoport |
| 2011/0304333 | A1 | | 12/2011 | Rapoport |
| 2012/0065491 | A1 | * | 3/2012 | Borgert et al. ................ 600/409 |
| 2012/0071745 | A1 | | 3/2012 | Rapoport |
| 2012/0073511 | A1 | | 3/2012 | Rapoport et al. |
| 2012/0077707 | A1 | | 3/2012 | Rapoport |
| 2012/0119742 | A1 | | 5/2012 | Rapoport |

(Continued)

*Primary Examiner* — Rodney Fuller

(57) ABSTRACT

An MRI device for providing high-contrast, high-resolution images of a fluid. The device includes: an envelope for at least partially confining the fluid; a plurality of magnets located at least partially around the envelope; and a CPU to process the images, including a computer readable medium containing instructions for generating at least one third image superimposing at least one image of the first images with at least one image of the second images, whereby a high-contrast, high-resolution real-time continuous images of the fluid is obtained.

35 Claims, 6 Drawing Sheets

(56) References Cited

U.S. PATENT DOCUMENTS

| | | | |
|---|---|---|---|
| 2012/0265050 A1* | 10/2012 | Wang | 600/411 |
| 2013/0009959 A1* | 1/2013 | Calamante et al. | 345/428 |
| 2013/0079624 A1 | 3/2013 | Rapoport | |
| 2013/0109956 A1 | 5/2013 | Rapoport | |
| 2013/0154644 A1* | 6/2013 | Virtanen et al. | 324/309 |
| 2013/0237803 A1 | 9/2013 | Rapoport | |
| 2013/0328560 A1 | 12/2013 | Rapoport | |
| 2013/0328563 A1 | 12/2013 | Rapoport | |
| 2014/0050827 A1 | 2/2014 | Rapoport | |
| 2014/0051973 A1 | 2/2014 | Rapoport et al. | |
| 2014/0051974 A1 | 2/2014 | Rapoport et al. | |
| 2014/0051976 A1 | 2/2014 | Rapoport et al. | |
| 2014/0099010 A1 | 4/2014 | Rapoport et al. | |
| 2014/0103927 A1 | 4/2014 | Rapoport | |
| 2014/0117989 A1 | 5/2014 | Rapoport | |
| 2014/0128725 A1 | 5/2014 | Rapoport et al. | |
| 2014/0139216 A1 | 5/2014 | Rapoport | |
| 2014/0142914 A1 | 5/2014 | Rapoport | |
| 2014/0152302 A1 | 6/2014 | Rapoport et al. | |
| 2014/0152310 A1 | 6/2014 | Rapoport | |
| 2014/0158062 A1 | 6/2014 | Rapoport et al. | |
| 2014/0230850 A1 | 8/2014 | Rapoport | |
| 2014/0266203 A1 | 9/2014 | Rapoport et al. | |
| 2014/0300358 A1 | 10/2014 | Rapoport | |
| 2014/0378821 A1 | 12/2014 | Rapoport et al. | |
| 2014/0378825 A1 | 12/2014 | Rapoport et al. | |
| 2015/0059655 A1 | 3/2015 | Rapoport | |

\* cited by examiner

HIGH RESOLUTION HIGH CONTRAST MRI FOR FLOWING MEDIA

FIELD OF THE INVENTION

The present invention generally pertains to a system and method for high resolution high contrast MRI for flowing media.

BACKGROUND OF THE INVENTION

It has long been known that low-field MRI produces high contrast images, but the weak field leads to a low signal to noise (S/N) ratio at poor resolution. Increasing the field increases the S/N ratio and, therefore, the resolution but decreases the contrast, so that high-field images have high resolution but poor contrast. There have been many attempts to overcome this limitation and to provide high-contrast high-resolution MRI images.

U.S. Pat. No. 5,168,226A to Hinks discloses a method whereby the total scan time may be shortened without losing resolution. The method disclosed in U.S. Pat. No. 516,226A comprises executing a fast spin echo pulse sequence in which a plurality of views are acquired and the fast spin echo pulse sequence is employed to acquire views from a plurality of separate images during a scan. The low-order phase encoding views are acquired for each image and stored in separate image data arrays, whereas the high-order phase encoding views are acquired only once and stored in all of the image data arrays. Each image data array is employed to reconstruct a separate image using standard reconstruction methods and apparatus. The desired T2 contrast is produced primarily by the low-order views of each image and the high-order views enhance the structural details of each image. Accordingly, only the low-order views need be acquired separately for each image to provide the desired T2 contrast, and a single set of high order phase encoding views can be used to fill in the structure details in all of the images. However, this method provides a relatively small enhancement of the contrast unless a large number of high-order phase encoding views are acquired.

Another method of improving contrast is by adding contrast agents to the region of interest, such as administration of a paramagnetic contrast agent (for example, gadolinium) to blood vessels and creating the MRI images at a time when the concentration of contrast agent is at a maximum. This method is disclosed in U.S. Pat. No. 5,479,925A to Dumoulin et al., among others. The method is adapted to enhancing contrast in medical MRI but has limited utility in industrial application where there are no obvious sub-domains (such as blood vessels in medical MRI) into which to introduce the contrast agents and where the presence of a contrast agent in a finished product may well be undesirable.

U.S. Patent Application US2004169512A to Jara discloses a method of combining three image-post-processing phases for the purpose of generating high-quality quantitative MR images (proton density (PD), T1, and T2) as well as high-quality virtual MR images with continuously adjustable computer-synthesized contrast weightings, from source images acquired directly with an MRI scanner. Each of the image-post-processing phases uses one or several new computer algorithms that improve image quality with respect to prior art, including linear-combination-of source-images (LCSI) algorithms for generating PD images and model-conforming algorithms for generating Q-MR images of tissue properties that influence NMR relaxation. However, the method depends on the presence of materials with different relaxation times in different parts of the scan (such as white matter and cerebrospinal fluid) to enable the enhanced contrast.

It is therefore a long felt need to provide an MRI device with provides high-contrast and high-resolution images.

SUMMARY OF THE INVENTION

It is an object of the present invention to disclose a system for high resolution high contrast MRI for flowing media.

It is another object of the present invention to disclose an MRI device for providing high contrast high resolution images of a fluid, comprising:
  a. an envelope for least partially confining said fluid;
  b. a plurality of magnets located at least partially around said envelope, said assembly comprising
     i. a least one first magnet configured to provide a high magnetic field for generating multiple time-resolved one or more first images at high resolution of at least a portion of said fluid; and
     ii. a least one second magnet configured to provide a low magnetic field for generating multiple time-resolved one or more second images at high contrast of at least portion of same said fluid; wherein at least one image of said first images and at least one image of said second images being generated in a time no greater than approximately the time between two first images; and
  c. a CPU to process said images comprising a computer readable medium containing instructions for generating at least one third image superimposing at least one image of said first images with at least one image of said second images, whereby a high-contrast, high-resolution real-time continuous image of said fluid is obtained.

It is another object of the present invention to disclose the MRI device, wherein said at least one first magnet is of 2 Tesla and lower.

It is another object of the present invention to disclose the MRI device, wherein said at least one first magnet is of 2 Tesla and higher.

It is another object of the present invention to disclose the MRI device, wherein said at least one first magnet is selected from a group consisting of permanent magnets, electromagnets, superconducting magnets, and any combination thereof.

It is another object of the present invention to disclose the MRI device, wherein said at least one second magnet is of 2 Tesla and lower.

It is another object of the present invention to disclose the MRI device, wherein said at least one second magnet is of 2 Tesla and higher.

It is another object of the present invention to disclose the MRI device, wherein said at least one second magnet is selected from a group consisting of permanent magnets, electromagnets, superconducting magnets, and any combination thereof.

It is another object of the present invention to disclose the MRI device, wherein said at least one high magnetic field magnet is said at least one low magnetic field magnet.

It is another object of the present invention to disclose the MRI device, wherein the angle between a perpendicular to the direction of flow and said high magnetic field is not the same as the angle between said perpendicular to the direction of flow and said low magnetic field.

It is another object of the present invention to disclose the MRI device, wherein an integrated MRI device comprises both said high magnetic field magnets and said low magnetic field magnets.

It is another object of the present invention to disclose the MRI device, wherein the MRI device comprises two MRI devices, one providing the high magnetic field magnets and one providing the low magnetic field magnets.

It is another object of the present invention to disclose the MRI device, wherein said high magnetic field magnets have a duty cycle greater than approximately 50% and said low magnetic fields magnets have a duty cycle less than approximately 50%.

It is another object of the present invention to disclose the MRI device, wherein said envelope is a member of a group consisting of a pipe, a duct, a tunnel, a conduit, a tube, a conveyor, a channel, a passage, and any combination thereof.

It is another object of the present invention to disclose the MRI device, wherein said envelope is an integral part of said MRI device.

It is another object of the present invention to disclose the MRI device, wherein said fluid is at least one of a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is another object of the present invention to disclose the MRI device, wherein said fluid is the fluid process stream in a production process.

It is another object of the present invention to disclose the MRI device, wherein said production process is in an industrial area, said industrial area a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI device, wherein said fluid purification is purification of water.

It is another object of the present invention to disclose the MRI device, wherein said fluid is contained within a bypass stream from a production line.

It is another object of the present invention to disclose the MRI device, wherein said fluid is the fluid process stream within a batch process.

It is another object of the present invention to disclose the MRI device, wherein said fluid is flowing within an engine or combustion chamber.

It is another object of the present invention to disclose the MRI device, wherein said fluid is the effluent from said engine or combustion chamber.

It is another object of the present invention to disclose the MRI device, wherein said fluid is some fraction of the effluent from said engine or combustion chamber.

It is another object of the present invention to disclose the MRI device, wherein said fluid is used in fertility treatments.

It is another object of the present invention to disclose the MRI device, wherein said fluid is used for artificial insemination.

It is another object of the present invention to disclose the MRI device, wherein said fluid contains liposomes.

It is another object of the present invention to disclose the MRI device, wherein said fluid is a part of an air curtain.

It is another object of the present invention to disclose the MRI device, wherein said fluid is a polymeric melt.

It is another object of the present invention to disclose the MRI device, wherein said polymeric melt is a member of a group consisting of rubbers, polyesters, polyamides, polypropylenes, polyethylenes, polyurethanes, and any combination thereof.

It is another object of the present invention to disclose the MRI device, wherein said device is part of an integrated analysis and production system for a product.

It is another object of the present invention to disclose the MRI device, wherein at least part of said integrated analysis and production system complies with a NeSSI specification.

It is another object of the present invention to disclose the MRI device, wherein at least part of said integrated analysis and production system complies with ANSI/ISA SP76.00.2002 miniature, modular mechanical standard specifications.

It is another object of the present invention to disclose the MRI device, wherein said fluid is a fluid within the body of a living subject.

It is another object of the present invention to disclose the MRI device, wherein said fluid flows from the body of a living subject, through said envelope, and is returned to said living subject.

It is another object of the present invention to disclose the MRI device, for imaging at least one first and at least one second image features; wherein said image processor is adapted to render said image by a Boolean method of correlating or combining said at least one first and at least one second image features.

It is another object of the present invention to disclose the MRI device, wherein said Boolean method uses Boolean operators selected from the group consisting of OR, AND, NOT, EXCLUSIVE OR, and any combination thereof.

It is another object of the present invention to disclose the MRI-based device described hereinabove, wherein the fluid is one of a group consisting of potable water, sewage, irrigation water, sea water, river water, lake water, industrial effluent, farm effluent, effluent from human habitation, road runoff, blood, lymph, a beverage, cleaning fluid, and any combination thereof.

It is another object of the present invention to disclose an MRI based method for providing high contrast high resolution images of a fluid, comprising:

a. providing an envelope for least partially confining said fluid;
b. providing a plurality of magnets located at least partially around said envelope, said assembly comprising
  i. a least one first magnet configured to provide a high magnetic field for generating multiple time-resolved one or more first images at high resolution of at least a portion of said fluid; and
  ii. a least one second magnet configured to provide a low magnetic field for generating multiple time-resolved one or more second images at high contrast of at least portion of same said fluid; wherein at least one image of said first images and at least one image of said second images being generated in a time no greater than approximately the time between two first images;
c. providing a CPU to process said images comprising a computer readable medium containing instructions for generating at least one third image superimposing at least one image of said first images with at least one image of said second images;
d. generating multiple time resolved one or more first images at high resolution of at least a portion of said fluid;
e. generating multiple time resolved one or more second images at high contrast of at least portion of same said fluid; and
f. superimposing at least one image of said first images with at least one image of said second images whereby a high-contrast, high resolution real-time continuous image of said fluid is obtained.

It is another object of the present invention to disclose the MRI based method, comprising an additional step of selecting said at least one first magnet to be of 2 Tesla and lower.

It is another object of the present invention to disclose the MRI based method, comprising an additional step of selecting said at least one first magnet to be of 2 Tesla and higher.

It is another object of the present invention to disclose the MRI based method, comprising an additional step of selecting said at least one first magnet from a group consisting of permanent magnets, electromagnets, superconducting magnets, and any combination thereof.

It is another object of the present invention to disclose the MRI based method, comprising an additional step of selecting said at least one second magnet to be of 2 Tesla and lower.

It is another object of the present invention to disclose the MRI based method, comprising an additional step of selecting said at least one second magnet to be of 2 Tesla and higher.

It is another object of the present invention to disclose the MRI based method, comprising an additional step of selecting said at least one second magnet from a group consisting of permanent magnets, electromagnets, superconducting magnets, and any combination thereof.

It is another object of the present invention to disclose the MRI based method, comprising an additional step of providing said at least one first magnet and said at least one second magnet as a single at least one magnet.

It is another object of the present invention to disclose the MRI based method, comprising an additional step of having the angle between a perpendicular to the direction of flow and said high magnetic field not the same as the angle between said perpendicular to the direction of flow and said low magnetic field.

It is another object of the present invention to disclose the MRI based method, comprising an additional step of selecting an integrated MRI device comprising both said high magnetic field magnets and said low magnetic field magnets.

It is another object of the present invention to disclose the MRI based method, comprising an additional step of selecting said MRI device comprising two MRI devices, one providing the high magnetic field magnets and one providing the low magnetic field magnets.

It is another object of the present invention to disclose the MRI based method, comprising an additional step of selecting a duty cycle for said high magnetic field magnets greater than approximately 50% and a duty cycle for said low magnetic fields magnets less than approximately 50%.

It is another object of the present invention to disclose the MRI based method, comprising an additional step of selecting said envelope from a group consisting of a pipe, a duct, a tunnel, a conduit, a tube, a conveyor, a channel, a passage, and any combination thereof.

It is another object of the present invention to disclose the MRI based method, comprising an additional step of forming said envelope as an integral part of at least one MRI device.

It is another object of the present invention to disclose the MRI based method, comprising an additional step of selecting said fluid from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is another object of the present invention to disclose the MRI based method, comprising an additional step of providing said fluid within the fluid process stream in a production process.

It is another object of the present invention to disclose the MRI based method, comprising an additional step of selecting said production process in an industrial area, said industrial area a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI based method, comprising an additional step of selecting water as the fluid purified in said fluid purification.

It is another object of the present invention to disclose the MRI based method, comprising an additional step of providing said fluid within a bypass stream from a production line.

It is another object of the present invention to disclose the MRI based method, comprising an additional step of providing said fluid in the fluid process stream within a batch process.

It is another object of the present invention to disclose the MRI based method, comprising an additional step of providing said fluid within an engine or combustion chamber.

It is another object of the present invention to disclose the MRI based method, comprising an additional step of providing said fluid as the effluent from said engine or combustion chamber.

It is another object of the present invention to disclose the MRI based method, comprising an additional step of providing said fluid as some fraction of the effluent from said engine or combustion chamber.

It is another object of the present invention to disclose the MRI based method, comprising an additional step of selecting a fluid used in fertility treatments.

It is another object of the present invention to disclose the MRI based method, comprising an additional step of selecting a fluid used for artificial insemination.

It is another object of the present invention to disclose the MRI based method, comprising an additional step of selecting a fluid containing liposomes.

It is another object of the present invention to disclose the MRI based method, comprising an additional step of selecting a fluid which is part of an air curtain.

It is another object of the present invention to disclose the MRI based method, comprising an additional step of selecting a fluid which is a polymeric melt.

It is another object of the present invention to disclose the MRI based method, comprising an additional step of selecting said polymeric melt from a group consisting of rubbers, polyesters, polyamides, polypropylenes, polyethylenes, polyurethanes, and any combination thereof.

It is another object of the present invention to disclose the MRI based method, comprising an additional step of integrating analysis and production of a product.

It is another object of the present invention to disclose the MRI based method, wherein least a part of said step of integrating analysis and production of a product complies with a NeSSI specification.

It is another object of the present invention to disclose the MRI based method, wherein at least a part of step of integrating analysis and production of a product complies with ANSI/ISA SP76.00.2002 miniature, modular mechanical standard specifications.

It is another object of the present invention to disclose the MRI based method, comprising an additional step of selecting a fluid within the body of a living subject as said flowing matter.

It is another object of the present invention to disclose the MRI based method, comprising an additional step of passing said fluid from the body of a living subject, through said envelope, and returning it to said living subject.

It is another object of the present invention to disclose the MRI based method, for imaging at least one first and at least one second image features; comprising an additional step of adapting said image processor to render said image by a Boolean method of correlating or combining said at least one first and at least one second image features.

It is another object of the present invention to disclose the MRI based method, comprising an additional step of selecting said Boolean operators of said Boolean method from the group consisting of OR, AND, NOT, EXCLUSIVE OR and any combination thereof.

It is another object of the present invention to disclose the MRI-based method as described hereinabove, comprising an additional step of selecting the fluid from a group consisting of potable water, sewage, irrigation water, sea water, river water, lake water, industrial effluent, farm effluent, effluent from human habitation, road runoff, blood, lymph, a beverage, cleaning fluid, and any combination thereof.

It is another object of the present invention to disclose an MRI-based system for providing high-contrast high-resolution images of a fluid comprising:
 a. the MRI device as defined hereinabove; and
 b. a fluid processing unit operation;
  wherein the operation provided by said fluid processing unit operation is continuously online feedbacked by means of said MRI device.

It is another object of the present invention to disclose the MRI-based system, wherein said fluid processing unit operation is one of a group consisting of mixing, kneading, transporting, analyzing, reacting, cooking, freezing, controlling the temperature, controlling the pressure, emulsifying, de-emulsifying, gelation, de-gelation, liquidizing, polymerizing, de-polymerizing, controlling viscosity, controlling density, controlling particulate concentration, controlling particulate size, controlling particulate density, creating a suspension, clearing a suspension from the fluid, assessing contaminant levels, clearing contaminants, and any combination thereof.

It is another object of the present invention to disclose the MRI-based system, wherein said feedbacking comprises one of a group consisting of altering temperature, altering pressure, altering volume, altering mixing speed, altering mixing time, altering flow rate, altering composition of at least one component of the fluid, altering particulate size, altering particulate density, altering levels of electromagnetic radiation, altering wavelengths of electromagnetic radiation, altering degree of filtration, altering method of filtration, adding filters, removing filters, changing filters, starting at least some portion of the fluid processing unit operation, stopping at least some portion of the fluid processing unit operation, and any combination thereof.

It is another object of the present invention to disclose an MRI based method for integrating analysis and production of a product, at least one step of said production comprising a fluid processing, comprising:
 a. providing the MRI device as defined hereinabove;
 b. providing a fluid processing unit operation;
 c. operating said fluid processing unit operation;
 d. continuously generating said first at least one images, said second at least one images and said third superimposed at least one images, such that a high-contrast, high resolution real-time continuous image of said fluid is obtained
 e. analyzing said images of fluid operated on by said fluid processing unit operation generated by said MRI device, whereby a high-contrast, high resolution real-time continuous image of said fluid is obtained; and
 f. feedbacking the results of said analysis to said fluid processing unit
  wherein the operation provided by said fluid processing unit operation is continuously online feedbacked by means of said MRI device.

It is another object of the present invention to disclose the MRI-based method, additionally comprising a step of selecting said fluid processing unit operation from a group consisting of mixing, kneading, transporting, analyzing, reacting, cooking, freezing, controlling the temperature, controlling the pressure, emulsifying, de-emulsifying, gelation, de-gelation, liquidizing, polymerizing, de-polymerizing, controlling viscosity, controlling density, controlling particulate concentration, controlling particulate size, controlling particulate density, creating a suspension, clearing a suspension from the fluid, assessing contaminant levels, clearing contaminants, and any combination thereof.

It is another object of the present invention to disclose the MRI-based method, additionally comprising a step of selecting said feedbacking from of a group consisting of altering temperature, altering pressure, altering volume, altering mixing speed, altering mixing time, altering flow rate, altering composition of at least one component of the fluid, altering particulate size, altering particulate density, altering levels of electromagnetic radiation, altering wavelengths of electromagnetic radiation, altering degree of filtration, altering method of filtration, adding filters, removing filters, changing filters, starting at least some portion of the fluid processing unit operation, stopping at least some portion of the fluid processing unit operation, and any combination thereof.

It is another object of the present invention to disclose an MRI-based system for screening for the presence of hazardous biological or chemical agent residues carried by an individual, comprising
 a. the MRI device as described hereinabove, said MRI device comprising an envelope for least partially confining a fluid;
 b. a fluid inlet in physical connection with said envelope;
 c. a fluid streamer for streaming a fluid over an individual passing through said fluid stream;
 d. a separator for separating out particles carried downstream by said fluid stream; and
 e. a particle collector for collecting said particles to provide a continuous fluid facilitated flow within said inlet to said envelope
  whereby a high-contrast, high resolution real-time continuous image of said fluid is obtained and the presence of said hazardous biological or chemical agent residues is indicated.

It is another object of the present invention to disclose the MRI-based system, wherein the type of hazardous biological or chemical agent residues carried by said individual is indicated.

It is another object of the present invention to disclose the MRI-based system, wherein said fluid stream is an air curtain.

It is another object of the present invention to disclose the MRI-based system, wherein said separating is facilitated by a cyclone or filter or both.

It is another object of the present invention to disclose the MRI-based system, wherein said collecting of said particles is facilitated by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose an MRI-based method for screening for the presence of hazardous biological or chemical agent residues carried by an individual, comprising
  a. providing the MRI device as defined hereinabove, said MRI device comprising an envelope for least partially confining a fluid;
  b. providing said MRI with a fluid inlet in physical connection with said envelope;
  c. providing a fluid stream for said individual to pass through;
  d. streaming fluid over said individual passing through said fluid stream;
  e. separating out particles carried downstream by said fluid stream;
  f. collecting said particles by a particle collecting means to provide a continuous fluid facilitated flow within said inlet to said envelope; and
  g. continuously generating first at least one images, second at least one images and third superimposed at least one images, such that a high-contrast, high resolution real-time continuous image of said fluid is obtained
  whereby the presence of said hazardous biological or chemical agent residues is indicated.

It is another object of the present invention to disclose the MRI-based method, comprising an additional step of indicating the type of hazardous biological or chemical agent residues carried by said individual.

It is another object of the present invention to disclose the MRI-based method, comprising an additional step of selecting said fluid stream to be an air curtain.

It is another object of the present invention to disclose the MRI-based method, comprising an additional step of facilitating said step of separating by means of a cyclone or filter or both.

It is another object of the present invention to disclose the MRI-based method, comprising an additional step of facilitating said step of collecting said particles by a particle collecting means selected from a group comprising activated carbon, a filter including air filter, water filter, paper filter, HEPA filter, micro-filter, water filter, water curtain, other conventional filter, other collection device, and any combination thereof.

It is another object of the present invention to disclose an MRI-based system for rapidly screening for the presence of hazardous biological or chemical residue in a flowing main fluid, comprising:
  a. the MRI device described hereinabove, said MRI device comprising an envelope for least partially confining a fluid;
  b. a main fluid;
  c. a purging device to separate at least one analyzable-size sample of fluid from said main fluid, said separator fluidly connected to said envelope;
  d. Functionalized Paramagnetic Particles (FPP) with a paramagnetic core and a moiety configured to interact with said biological or chemical agent residues;
  e. means for mixing said FPP with said at least one analyzable-size sample of fluid; and
  f. a facilitator to facilitate flow of said fluid mixed with said FPP through said MRI device;
  whereby a high-contrast, high-resolution real-time continuous image of said at least one analyzable-size sample of said fluid is obtained, and further whereby the presence of said hazardous biological or chemical agent residues in said main fluid is indicated.

It is another object of the present invention to disclose the MRI-based system, wherein said step of separating is facilitated by means of a cyclone or filter or both.

It is another object of the present invention to disclose the MRI-based system, wherein said step of collecting said particles is facilitated by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose the MRI-based system, wherein the type of hazardous biological or chemical agent residues in said main fluid is indicated.

It is another object of the present invention to disclose the MRI-based system, wherein the fluid is one of a group consisting of potable water, sewage, irrigation water, sea water, river water, lake water, industrial effluent, farm effluent, effluent from human habitation, road runoff, blood, lymph, a beverage, cleaning fluid, and any combination thereof.

It is another object of the present invention to disclose an MRI-based method for rapidly screening for the presence of hazardous biological or chemical residue in a flowing main fluid, comprising:
  a. providing the MRI device as described above;
  b. purging said main fluid to an analyzable-size sample;
  c. facilitatedly flowing said purged fluid through said MRI;
  d. providing Functionalized Paramagnetic Particles (FPP) with a paramagnetic core and a moiety configured to interact with said biological or chemical agent residues;
  e. introducing said FPP within said purged fluid,
  f. if said hazardous biological or chemical residue is present in said purged fluid, then interacting said FPP with said biological or chemical agent residues;
  a. generating multiple time resolved one or more first images at high resolution of at least a portion of said purged fluid;
  b. generating multiple time resolved one or more second images at high contrast of at least portion of same said purged fluid;
  g. superimposing at least one image of said first images with at least one image of said second images whereby a high-contrast, high resolution real-time continuous image of said purged fluid is obtained;
  h. measuring a change in a nuclear relaxation property of said purged fluid caused by said interaction between said FPP and said biological or chemical agent residues in the applied magnetic field, as indicated by said high-contrast, high resolution real-time continuous image of said purged fluid; and
  i. correlating said change to the presence of said biological or chemical agent residues in said purged fluid,
  whereby the presence of said hazardous biological or chemical agent residues in said main fluid is indicated.

It is another object of the present invention to disclose the MRI-based method, additionally comprising a step of facilitating said step of separating by means of a cyclone or filter or both.

It is another object of the present invention to disclose the MRI-based method, wherein said step of collecting said particles is facilitated by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose the MRI-based method, additionally comprising a step of indicating the type of hazardous biological or chemical agent residues in said main fluid.

It is another object of the present invention to disclose the MRI-based method, additionally comprising a step of selecting the fluid to be one of a group consisting of potable water, sewage, irrigation water, sea water, river water, lake water, industrial effluent, farm effluent, effluent from human habitation, road runoff, blood, lymph, a beverage, cleaning fluid, and any combination thereof.

BRIEF DESCRIPTION OF THE FIGURES

In order to better understand the invention and its implementation in practice, a plurality of embodiments will now be described, by way of non-limiting example only, with reference to the accompanying drawings, wherein.

DETAILED DESCRIPTION OF THE PREFERRED EMBODIMENTS

Figure 1:
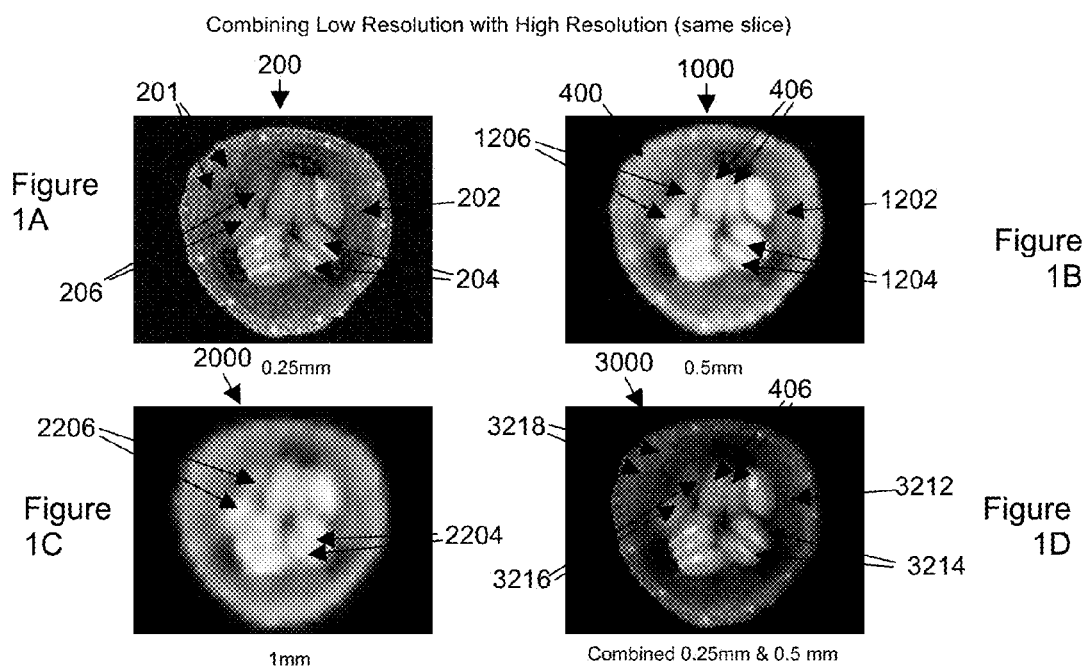
FIGS. 1A, 1B, 1C and 1D depict MRI images of a cross sectional slice of a cucumber typically generated by the low intensity magnetic field device at different in-slice pixel sizes, respectively, in accordance with a preferred embodiment of the present invention.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing superimposed high resolution high contrast MRI images for flowing media.

As used herein, the term 'plurality' refers in a non-limiting manner to any integer equal to or greater than 1.

The term 'about' refers herein a value being ±25% of the defined measure.

The term 'approximately' refers herein a value being ±25% of the defined measure.

The term 'rapidly' refers herein to a time interval of less than 5 minutes.

The term 'nearly contemporaneously' refers to a time interval less than the time interval between generation of successive first images.

The term 'duty cycle' refers to the fraction of time during which a device is operated.

It is thus according to one embodiment of the invention wherein superimposed MRI scanning systems are disclosed. Those systems comprise, inter alia, at least one high resolution MRI device, having means to scan high field, low contrast (HFLC) images, e.g., a commercially available 7 Tesla MRI device (hereinafter HFLC-MRI), and at least one low resolution MRI device, having means to scan low field, high contrast (LFHC) images, e.g., a commercially available Aspect Magnet Technologies Ltd. products (See company site at http://aspect-mr.com) 1 Tesla MRI device (hereinafter LFHC-MRI).

In another, preferred, embodiment of the system, the MRI images are generated continuously. Each HFLC image is followed by one or more LFHC images, so that the HFLC and LFHC images are nearly contemporaneous.

In preferred embodiments, high magnetic fields will be produced for a larger fraction of the operating time than low magnetic field will be. For non-limiting example, in an MRI-based device with separate magnets for producing HFLC images and for producing LFHC magnets, the fluid would be exposed to a high magnetic field for 90% of the time, while it would be exposed to a low magnetic field for only 10% of the time.

In another embodiment, the HFLC and LFHC images are generated concurrently, for at least part of their duty cycle.

It is according to yet another embodiment of the invention wherein MRI super-imposing scanning methods are disclosed. Those methods comprise, inter alia, steps of obtaining at least one high resolution high field, low contrast (HFLC) scan, e.g., by means of the aforesaid commercially available 7 Tesla MRI devices (hereinafter HFLC-images); further obtaining at least one low resolution low field, high contrast LFHC scan (hereinafter LFHC-images), by means of e.g., one of the commercially available Aspect Magnet Technologies Ltd products 1 Tesla MRI devices (hereinafter LFHC-scans); and superimposing said at least one HFLC-images and said LFHC-images such that one or more superimposed high resolution high contrast images is obtained.

In another embodiment, a purpose-built device integrates both the high-field scanning system and the low-field scanning system. In such a purpose-built device, a single RF coil or RF probe can be used to measure the magnetic fields generating the HFLC and LFHC images, and only a single imaging chamber, CPU, etc. are needed.

Methods of superimposing the HFLC and LFHC scans include registering and aligning the images, also thresh-holding, region growing, and editing. Registering and aligning techniques include rendering the images using Boolean methods of correlating and combining the images. Combining binary images using Boolean logic makes it possible to select structures or objects based on multiple criteria, such as, but not limited to, masking and thresh-holding. The Boolean operators commonly used are OR, AND, NOT, EXCLUSIVE OR and combinations thereof.

Reference is now made to FIGS. 1A, 1B, 1C and 1D, which show MRI images of a cross sectional slice of a cucumber typically generated by the low intensity magnetic field device at different in-slice pixel sizes, respectively, in accordance with a preferred embodiment of the present invention;

FIG. 1A shows the cross section image of the cucumber 200 generated at an in-slice pixel size of 0.25 mm (high resolution) and a group of cucumber seeds 204 are clearly distinguishable from a cucumber background 202. However, due to the low SNR, the image of the cucumber seeds 204 is not clearly distinguishable from the cucumber background 202. A group of seeds 206 are not clearly distinguishable from the background 202. In addition, FIG. 1A shows a group of seeds 201 located on the periphery of the cucumber 200.

FIG. 1B shows a cross section image of the cucumber 1000 generated at an in-slice pixel size of 0.5 mm (medium resolution) and the group of seeds 1204 is clearly imaged. The image of the group of seeds 1206 is clearer. Due to edge effects, the border between the cucumber flesh 1202 and the group of cucumber seeds 1204 is not clearly defined. The group 1206 is not clearly distinguishable from the cucumber background 1202. Due to the decrease in the resolution, FIG. 1B does not clearly identify a group of seeds located on the periphery of the cucumber 1000.

FIG. 1C shows a cross section image of the cucumber 2000 generated at an in-slice pixel size of 1 mm (low resolution) and groups of cucumber seeds 2204 and 2206 are not clearly seen and the image is very blurred. Due to the further decrease in the resolution, FIG. 1C does not clearly identify a group of seeds located on the periphery of the cucumber 2000.

FIG. 1D shows a combined image 3000 of the high resolution (0.25 in-slice pixel size) and medium resolution (0.5 mm in-slice pixel size). The group of seeds 3214 is distinguishable from the cucumber background 3212 and the group of seeds 3216 is barely distinguishable from the cucumber background 3212. However, due to noise, the edges of the seeds 3214 and 3216 are not clearly discernible. FIG. 1D shows a group of seeds 3218 located on the periphery of the cucumber 3000. To summarize, the resolution in 3000 in FIG. 1D has the full resolution of cucumber 200 in FIG. 1A.

Figure 2A:
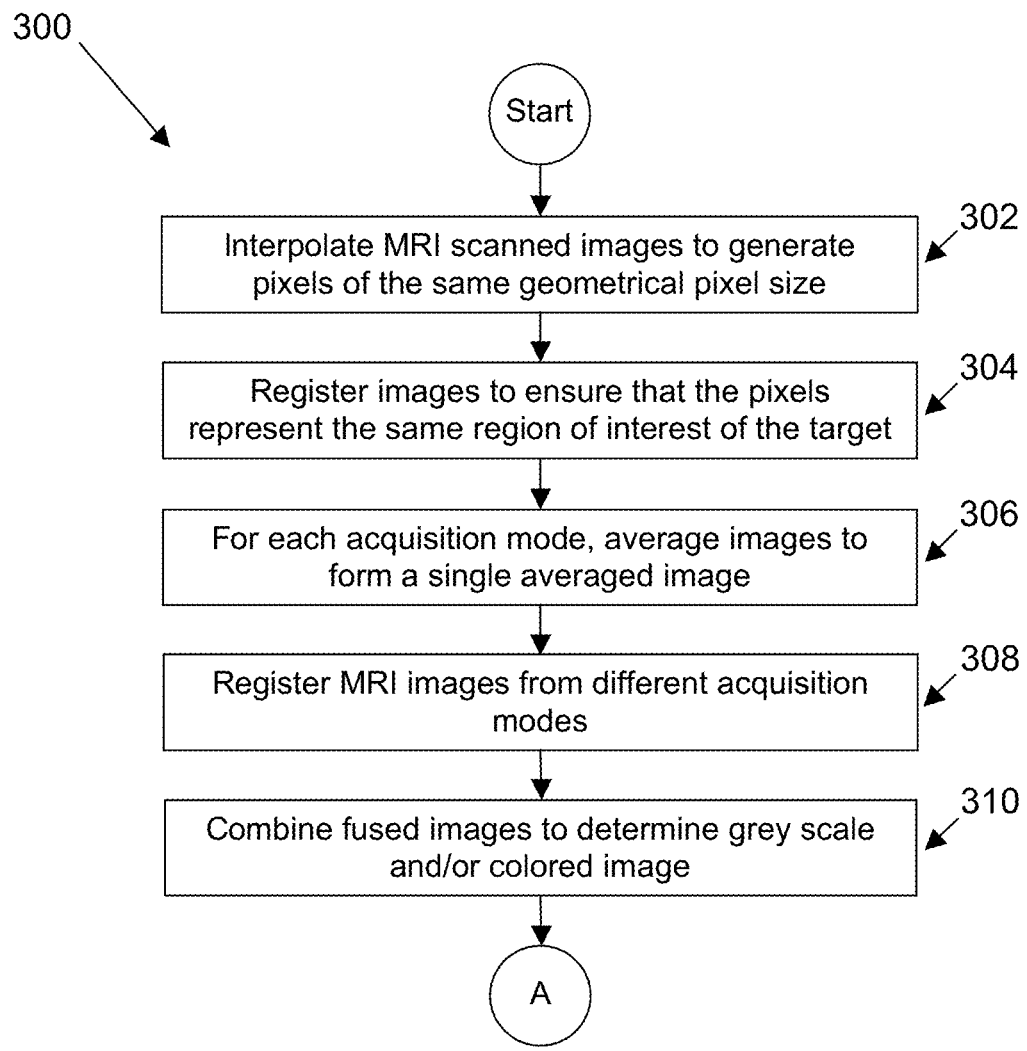
FIGS. 2A and 2B present a flow chart of a typical procedure for fusing multiple sets of images of a given volume of the target into a single enhanced image, in accordance with a preferred embodiment of the present invention.
Figure 2B:
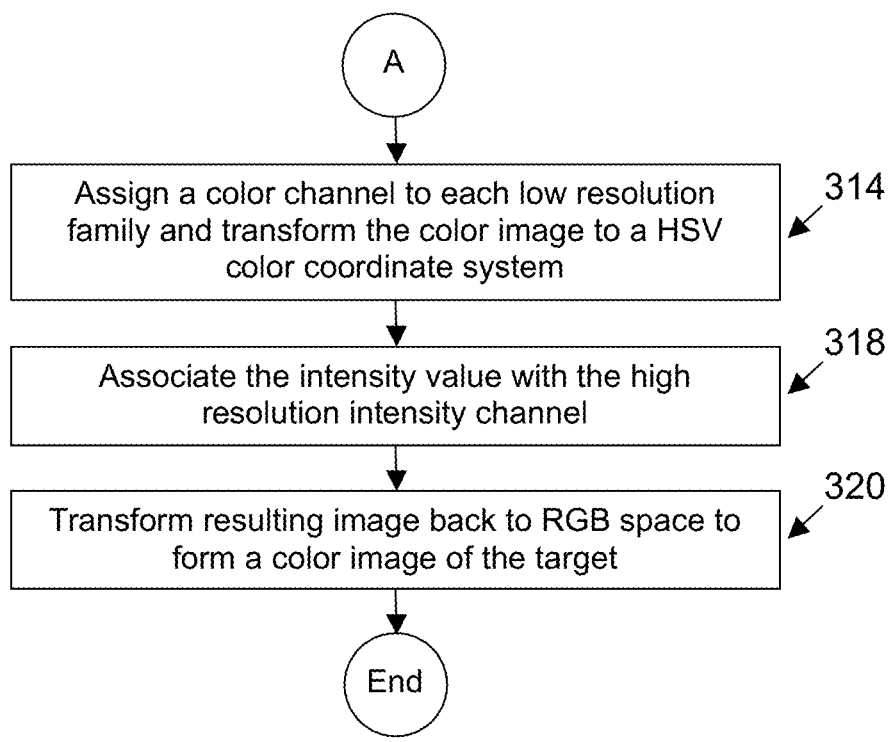

Reference is now made to FIGS. 2A and 2B, which present a flow chart of a typical procedure 300 for fusing multiple sets of images of a given volume into a single enhanced image, in accordance with a preferred embodiment of the present invention. The procedure 300 is controlled by a processing unit, wherein the images are taken at the same slice of a solid target.

In step 302, the MRI scanned images are interpolated in order to generate voxels of the same geometrical voxel size, as is known in the art.

In step 304, registration of the images acquired from the same acquisition mode is performed. The registration procedure ensures that the voxel representations of the images to be fused represent the same region of interest of the target.

In step 306, the registered images are averaged to form a single image for each acquisition mode. This image includes a multiplicity of slices.

In step 308, the combined images from the distinct acquisition modes used to image the registered target. A typical registration method is "The Lukas-Kanade Optical Flow Method", as is known in art and described in "An Iterative Image Registration Technique with an Application to Stereo Vision", B. D. Lucas and T. Kanade (1981), published in the Proceedings of Imaging Understanding Workshop, pages 121-130. Since the distinct image acquisition modes may have a different appearance, other methods known in the art for registering multi-modality images may be used. These can be based on maximizing mutual information of images patches as is known in the art.

In step 310, the registered MR images of different acquisition modes are fused according to any of the well known fusion methods. In the following steps of FIG. 2A, a method that is suited to variable resolution images acquisitions is outlined:

In order to fuse the different acquisition modes of averaged images, the images are divided into two types: high resolution images and low resolution images. The high resolution images are combined to form a single monochrome image as follows:

The pixel values are combined using some weighting, which can be assigned by a variety of methods, such as a principal component analysis. Principal component analysis is known in the art and is described in "Principal Component Analysis", by I. T. Jolliffe, Series: Springer Series in Statistics, 2nd ed., Springer, N.Y., 2002, XXIX, 487 p. 28 illus. ISBN 978-0-387-95442-4. This combined monochrome image controls the brightness and/or intensity of the fused colored image while the low resolution images will control the spectral resolution of the fused image.

The steps for fusing these high resolution and low resolution images to form a colored image are further outlined in FIG. 2B.

In step 314, each low-resolution image acquisition mode is assigned a color channel: for example, red, green and blue, for three acquisition modes. The low resolution image is transformed to the HSV (hue, saturation, value) basis.

In step 318, the intensity channel (value) is associated with the high resolution monochrome image and/or combined with the low-resolution intensity channel, for example by the Brovey method, as is known in the art.

In step 320, the resulting image is transformed back to RGB space to form a colored fused final image of the target.

Reference is now made to FIGS. 3A-3D, which compare, in grey and color, the results of combining multi-resolution images as grey and color images, in accordance with a preferred embodiment of the present invention.

Figure 3:
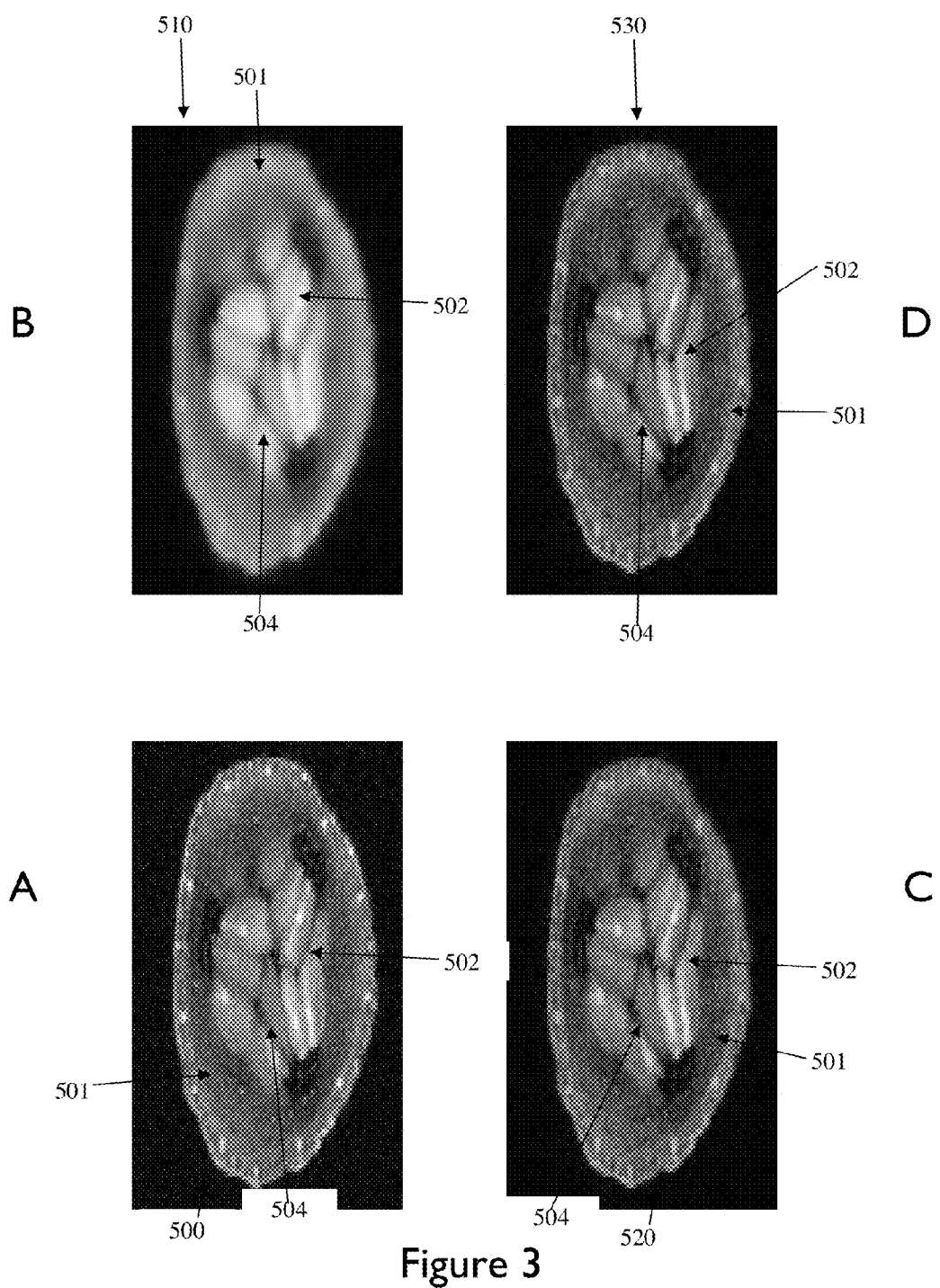
FIGS. 3A-3C compare in grey and color, the results of combining multi-resolutions images as grey and color images, in accordance with a preferred embodiment of the present invention.

FIG. 3A shows a high resolution image 500 of a cross section of a cucumber 501 and groups of cucumber seeds 502 and 504. FIG. 3A is similar to the high resolution scan shown in FIG. 1A.

FIG. 3B shows a high resolution image 520 of a cross section of the cucumber 501 and groups of cucumber seeds 502 and 504. In the image 510, the high resolution image (FIG. 1A), the medium resolution image (FIG. 1B) and the low resolution image (FIG. 1C) are combined by a IHS method as described in "Application of the IHS Color Transform to the Processing of Multisensor Data and Image Enhancement", (Haydn, R., Dalke, G. W. and Henkel, J.: Proc. of the International Symposium on Remote Sensing of Arid and Semiarid Lands, Cairo, pp. 599-616, 1982.), The high resolution image 520 is clearer than the colored image 510.

FIG. 3C shows a high resolution image 520 of a cross section of the cucumber 501 and groups of cucumber seeds 502 and 504. In the image 520, the high resolution image (FIG. 1A), the medium resolution image (FIG. 1B) and the low resolution image (FIG. 1C) are combined by the Brovey method, as is known in the art (step 314, FIG. 2A). The image 530 clearly distinguishes between the groups of cucumber seeds 502 and 504 and the groups of cucumber seeds 502 and 504 are clearly distinguishable from the cucumber background 501.

The present system can be used where the analyzed objects are selected from agricultural raw materials or products, preferably fluid products, cosmetics, chemicals, powders, gases, medicaments, industrial matters, or any other flowable combination of solid, liquid and gas.

In another embodiment of the present invention, the fluid is contained in a pipe or conduit which passes through the volume of the high magnetic field and the low magnetic field MRI scans.

Figure 4:
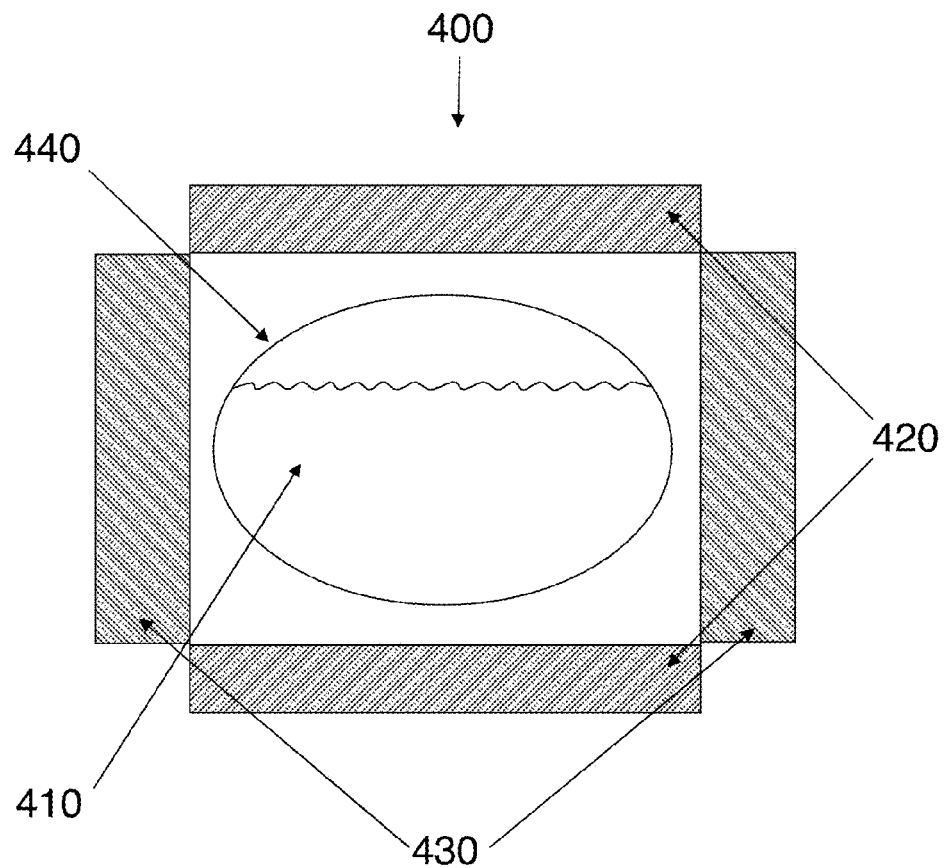
FIG. 4 schematically illustrates an embodiment with the envelope for the fluid part of an MRI device.
Figure 5:
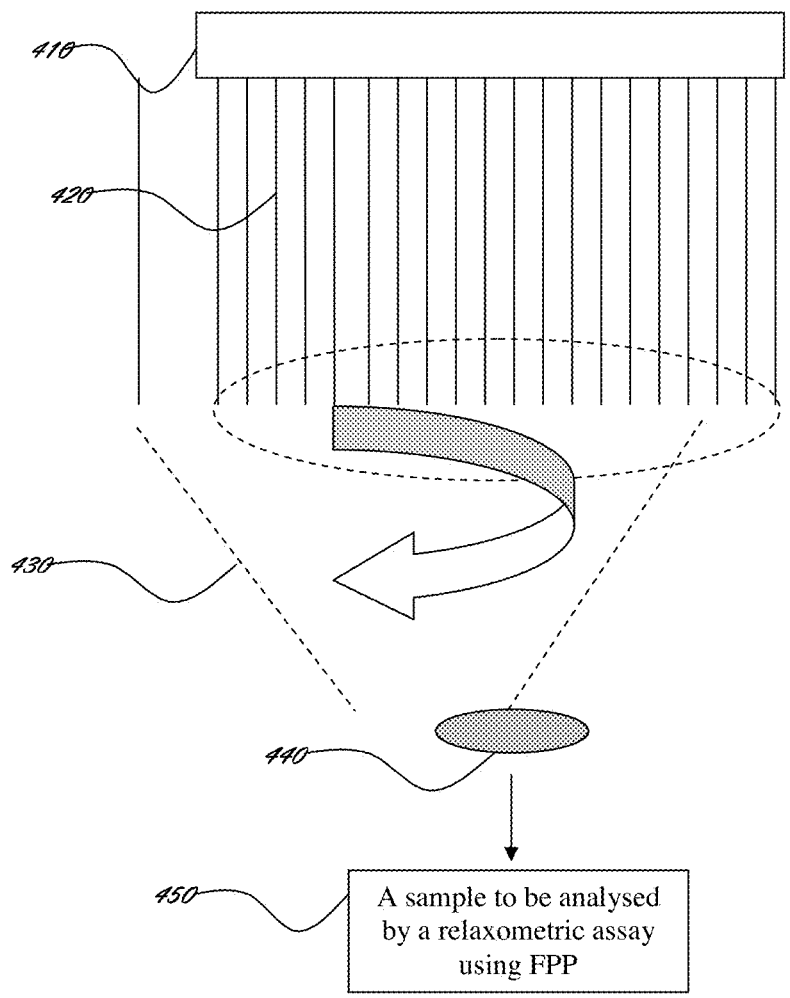
FIG. 5 schematically illustrates embodiments of a system rapidly screening for the presence of hazardous biological or chemical agent residues carried by an individual.

In another embodiment, the envelope for the fluid in the region of the volume of the high magnetic field and low-field MRI scans is the MRI itself. A non-limiting example of an embodiment of this type is schematically illustrated in FIG. 4. The device (400) comprises two sets of magnets (420, 430).

The RF coils (not shown) are part of an envelope (440) which contains the fluid (410). In this embodiment, the high magnetic field magnets (420) are in a horizontal orientation, while the low magnetic field magnets (420) are in a vertical orientation. In other embodiments, the low field magnets can be inside the high magnetic field magnets. In yet other embodiments, the low magnetic field magnets can be outside the high magnetic field magnets.

In some embodiments, the two sets of magnets form part of a single, integrated device. In other embodiments, each set of magnets is part of a separate device, such as the commercially available devices described hereinabove.

EXAMPLE 1

Use of the system and method of the present invention for screening passengers carrying hazardous biological or chemical agent residues in airports:

It is within the scope of the present invention to provide means and methods for screening passengers, for example in the airport, for hazardous biological or chemical agent residues they may be carrying. A non-limiting example of such an agent is a disease pathogen. Another non-limiting example is a nerve gas such as Sarin or explosive residue. Such a screening system and method may be applied in main junctions such as airports and public places.

According to one embodiment, the method and system for rapidly screening for the presence of hazardous biological or chemical agent residues, for example, a contagious disease-causing pathogen carried by an individual, can be used in homeland security. The MRI-based system of the present invention can be combined with a technique using functionalized paramagnetic particles (FPP) configured to interact with a target biochemical molecule, each FPP comprising a paramagnetic core and a moiety configured to interact with a target biochemical molecule. This technique can fish out and detect biological or chemical agents such as pathogens and/or minuscule amounts of DNA or other residue, marker or particulate of a biological or chemical agent. In one embodiment, the FPP are configured, i.e., by a chemical modification, to specifically bind to a residue or marker or any part that is unique to a particular biological or chemical agent. When the FPP bind to the marker or residue of the biological or chemical agent, a magnetic resonance signal is detected, which is amplified by the water molecules that surround the FPP? Then the change in the magnetic signature measured by the MRI-based system of the present invention can be detected on a computer screen or portable electronic device, such as a smartphone, and determination be made whether the sample is infected with a particular pathogen or contains residues of a hazardous biological or chemical agent.

The method of the present invention can be used for screening passengers, for example in the airport, to determine if they are carrying (innocently or otherwise) residues of a hazardous biological or chemical agent, such as a contaminating disease-causing pathogen or particles thereof, and thereby prevent the spread of the disease before it becomes a pandemic. A typical test which may be applied in airports, for example, is schematically described in FIG. 5, showing the following embodiments and steps:

A passenger is asked to pass through air stream 420 generated by an air curtain 410. As used herein the term 'air curtain' refers to a fan-powered device or the like. A common configuration for an air curtain is a downward-facing blower fan that blows air across a defined surface. The fan should be powerful enough to generate a jet of air that can reach the floor.

According to a further embodiment, particles carried by the air stream 420 are then separated downstream, using separation means, preferably using a cyclonic separation means 430. It is acknowledged that a cyclonic separation system is herein refers to a means for removing particulates from an air, gas or liquid stream, through vortex separation. The rotational effects and gravity are used to separate mixtures of solids and fluids. The particles that are carried out by the air stream 420 may include pathogens and/or debris, residues or particles of a biological or chemical agent with which the passenger has been in recent contact.

According to a further embodiment, the particles carried on the separated downstream air are collected by a particle collecting means 440 (such as activated carbon, a filter, HEPA filter, microfilter, water filter, air filter or water curtain, or any other conventional filter or collection device) to obtain a sample for analysis 450. The sample containing the separated particles or residues 450 is then subjected to a relaxometric assay using an FPP-based amplification technology, configured to detect the presence of small amounts of hazardous biological or chemical agent residues. By measuring a change in a nuclear relaxation property of the sample caused by the interaction between the FPP and the biological or chemical agent residues or part thereof, in the applied magnetic field, small amounts of a hazardous biological or chemical agent carried by an individual can be detected, and the matter investigated further. In this embodiment, detection is accomplished in less than about a minute, as this is a not unacceptable time for passage of a passenger through a screening device.

In another embodiment, a fluid, such as potable water in a national or local water carrier system, can be screened for small amounts of a hazardous biological or chemical agent. In this embodiment, the water is continuously sampled, with analyzable samples flowing through the MRI-based device of the present invention. FPP are added to the flowing samples. If there are hazardous biological or chemical agents present, they react with the FPP and are detected by the MRI as described hereinabove. In this embodiment, it is feasible for detection to take several minutes.

It is another object of the present invention to disclose an MRI device for providing high contrast high resolution images of a fluid, comprising:

a. an envelope for least partially confining said fluid;

b. a plurality of magnets located at least partially around said envelope, said assembly comprising i. a least one first magnet configured to provide a high magnetic field for generating multiple time-resolved one or more first images at high resolution of at least a portion of said fluid; and ii. a least one second magnet configured to provide a low magnetic field for generating multiple time-resolved one or more second images at high contrast of at least portion of same said fluid; wherein at least one image of said first images and at least one image of said second images being generated in a time no greater than approximately the time between two first images; and c. a CPU to process said images comprising a computer readable medium containing instructions for generating at least one third image superimposing at least one image of said first images with at least one image of said second images, whereby a high-contrast, high-resolution real-time continuous image of said fluid is obtained.

It is another object of the present invention to disclose the MRI device, wherein said at least one first magnet is of 2 Tesla and lower.

It is another object of the present invention to disclose the MRI device, wherein said at least one first magnet is of 2 Tesla and higher.

It is another object of the present invention to disclose the MRI device, wherein said at least one first magnet is selected from a group consisting of permanent magnets, electromagnets, superconducting magnets, and any combination thereof.

It is another object of the present invention to disclose the MRI device, wherein said at least one second magnet is of 2 Tesla and lower.

It is another object of the present invention to disclose the MRI device, wherein said at least one second magnet is of 2 Tesla and higher.

It is another object of the present invention to disclose the MRI device, wherein said at least one second magnet is selected from a group consisting of permanent magnets, electromagnets, superconducting magnets, and any combination thereof.

It is another object of the present invention to disclose the MRI device, wherein said at least one high magnetic field magnet is said at least one low magnetic field magnet.

It is another object of the present invention to disclose the MRI device, wherein the angle between a perpendicular to the direction of flow and said high magnetic field is not the same as the angle between said perpendicular to the direction of flow and said low magnetic field.

It is another object of the present invention to disclose the MRI device, wherein an integrated MRI device comprises both said high magnetic field magnets and said low magnetic field magnets.

It is another object of the present invention to disclose the MRI device, wherein the MRI device comprises two MRI devices, one providing the high magnetic field magnets and one providing the low magnetic field magnets.

It is another object of the present invention to disclose the MRI device, wherein said high magnetic field magnets have a duty cycle greater than approximately 50% and said low magnetic fields magnets have a duty cycle less than approximately 50%.

It is another object of the present invention to disclose the MRI device, wherein said envelope is a member of a group consisting of a pipe, a duct, a tunnel, a conduit, a tube, a conveyor, a channel, a passage, and any combination thereof.

It is another object of the present invention to disclose the MRI device, wherein said envelope is an integral part of said MRI device.

It is another object of the present invention to disclose the MRI device, wherein said fluid is at least one of a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is another object of the present invention to disclose the MRI device, wherein said fluid is the fluid process stream in a production process.

It is another object of the present invention to disclose the MRI device, wherein said production process is in an industrial area, said industrial area a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI device, wherein said fluid purification is purification of water.

It is another object of the present invention to disclose the MRI device, wherein said fluid is contained within a bypass stream from a production line.

It is another object of the present invention to disclose the MRI device, wherein said fluid is the fluid process stream within a batch process.

It is another object of the present invention to disclose the MRI device, wherein said fluid is flowing within an engine or combustion chamber.

It is another object of the present invention to disclose the MRI device, wherein said fluid is the effluent from said engine or combustion chamber.

It is another object of the present invention to disclose the MRI device, wherein said fluid is some fraction of the effluent from said engine or combustion chamber.

It is another object of the present invention to disclose the MRI device, wherein said fluid is used in fertility treatments.

It is another object of the present invention to disclose the MRI device, wherein said fluid is used for artificial insemination.

It is another object of the present invention to disclose the MRI device, wherein said fluid contains liposomes.

It is another object of the present invention to disclose the MRI device, wherein said fluid is a part of an air curtain.

It is another object of the present invention to disclose the MRI device, wherein said fluid is a polymeric melt.

It is another object of the present invention to disclose the MRI device, wherein said polymeric melt is a member of a group consisting of rubbers, polyesters, polyamides, polypropylenes, polyethylenes, polyurethanes, and any combination thereof.

It is another object of the present invention to disclose the MRI device, wherein said device is part of an integrated analysis and production system for a product.

It is another object of the present invention to disclose the MRI device, wherein at least part of said integrated analysis and production system complies with a NeSSI specification.

It is another object of the present invention to disclose the MRI device, wherein at least part of said integrated analysis and production system complies with ANSI/ISA SP76.00.2002 miniature, modular mechanical standard specifications.

It is another object of the present invention to disclose the MRI device, wherein said fluid is a fluid within the body of a living subject.

It is another object of the present invention to disclose the MRI device, wherein said fluid flows from the body of a living subject, through said envelope, and is returned to said living subject.

It is another object of the present invention to disclose the MRI device, for imaging at least one first and at least one second image features; wherein said image processor is adapted to render said image by a Boolean method of correlating or combining said at least one first and at least one second image features.

It is another object of the present invention to disclose the MRI device, wherein said Boolean method uses Boolean operators selected from the group consisting of OR, AND, NOT, EXCLUSIVE OR, and any combination thereof.

It is another object of the present invention to disclose the MRI-based device described hereinabove, wherein the fluid is one of a group consisting of potable water, sewage, irrigation water, sea water, river water, lake water, industrial effluent, farm effluent, effluent from human habitation, road run-off, blood, lymph, a beverage, cleaning fluid, and any combination thereof.

It is another object of the present invention to disclose an MRI based method for providing high contrast high resolution images of a fluid, comprising:
a. providing an envelope for least partially confining said fluid;
b. providing a plurality of magnets located at least partially around said envelope, said assembly comprising
   i. a least one first magnet configured to provide a high magnetic field for generating multiple time-resolved one or more first images at high resolution of at least a portion of said fluid; and
   ii. a least one second magnet configured to provide a low magnetic field for generating multiple time-resolved one or more second images at high contrast of at least portion of same said fluid; wherein at least one image of said first images and at least one image of said second images being generated in a time no greater than approximately the time between two first images;
c. providing a CPU to process said images comprising a computer readable medium containing instructions for generating at least one third image superimposing at least one image of said first images with at least one image of said second images;
d. generating multiple time resolved one or more first images at high resolution of at least a portion of said fluid;
e. generating multiple time resolved one or more second images at high contrast of at least portion of same said fluid; and
f. superimposing at least one image of said first images with at least one image of said second images
whereby a high-contrast, high resolution real-time continuous image of said fluid is obtained.

It is another object of the present invention to disclose the MRI based method, comprising an additional step of selecting said at least one first magnet to be of 2 Tesla and lower.

It is another object of the present invention to disclose the MRI based method, comprising an additional step of selecting said at least one first magnet to be of 2 Tesla and higher.

It is another object of the present invention to disclose the MRI based method, comprising an additional step of selecting said at least one first magnet from a group consisting of permanent magnets, electromagnets, superconducting magnets, and any combination thereof.

It is another object of the present invention to disclose the MRI based method, comprising an additional step of selecting said at least one second magnet to be of 2 Tesla and lower.

It is another object of the present invention to disclose the MRI based method, comprising an additional step of selecting said at least one second magnet to be of 2 Tesla and higher.

It is another object of the present invention to disclose the MRI based method, comprising an additional step of selecting said at least one second magnet from a group consisting of permanent magnets, electromagnets, superconducting magnets, and any combination thereof.

It is another object of the present invention to disclose the MRI based method, comprising an additional step of providing said at least one first magnet and said at least one second magnet as a single at least one magnet.

It is another object of the present invention to disclose the MRI based method, comprising an additional step of having the angle between a perpendicular to the direction of flow and said high magnetic field not the same as the angle between said perpendicular to the direction of flow and said low magnetic field.

It is another object of the present invention to disclose the MRI based method, comprising an additional step of selecting an integrated MRI device comprising both said high magnetic field magnets and said low magnetic field magnets.

It is another object of the present invention to disclose the MRI based method, comprising an additional step of selecting said MRI device comprising two MRI devices, one providing the high magnetic field magnets and one providing the low magnetic field magnets.

It is another object of the present invention to disclose the MRI based method, comprising an additional step of selecting a duty cycle for said high magnetic field magnets greater than approximately 50% and a duty cycle for said low magnetic fields magnets less than approximately 50%.

It is another object of the present invention to disclose the MRI based method, comprising an additional step of selecting said envelope from a group consisting of a pipe, a duct, a tunnel, a conduit, a tube, a conveyor, a channel, a passage, and any combination thereof.

It is another object of the present invention to disclose the MRI based method, comprising an additional step of forming said envelope as an integral part of at least one MRI device.

It is another object of the present invention to disclose the MRI based method, comprising an additional step of selecting said fluid from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is another object of the present invention to disclose the MRI based method, comprising an additional step of providing said fluid within the fluid process stream in a production process.

It is another object of the present invention to disclose the MRI based method, comprising an additional step of selecting said production process in an industrial area, said industrial area a member of a group consisting of the pharmaceuticals, food production, beverage production, chemical refining, chemical processing, medical products, biological products, metal casting, metal refining, desalination, fluid purification, and sewage processing.

It is another object of the present invention to disclose the MRI based method, comprising an additional step of selecting water as the fluid purified in said fluid purification.

It is another object of the present invention to disclose the MRI based method, comprising an additional step of providing said fluid within a bypass stream from a production line.

It is another object of the present invention to disclose the MRI based method, comprising an additional step of providing said fluid in the fluid process stream within a batch process.

It is another object of the present invention to disclose the MRI based method, comprising an additional step of providing said fluid within an engine or combustion chamber.

It is another object of the present invention to disclose the MRI based method, comprising an additional step of providing said fluid as the effluent from said engine or combustion chamber.

It is another object of the present invention to disclose the MRI based method, comprising an additional step of providing said fluid as some fraction of the effluent from said engine or combustion chamber.

It is another object of the present invention to disclose the MRI based method, comprising an additional step of selecting a fluid used in fertility treatments.

It is another object of the present invention to disclose the MRI based method, comprising an additional step of selecting a fluid used for artificial insemination.

It is another object of the present invention to disclose the MRI based method, comprising an additional step of selecting a fluid containing liposomes.

It is another object of the present invention to disclose the MRI based method, comprising an additional step of selecting a fluid which is part of an air curtain.

It is another object of the present invention to disclose the MRI based method, comprising an additional step of selecting a fluid which is a polymeric melt.

It is another object of the present invention to disclose the MRI based method, comprising an additional step of selecting said polymeric melt from a group consisting of rubbers, polyesters, polyamides, polypropylenes, polyethylenes, polyurethanes, and any combination thereof.

It is another object of the present invention to disclose the MRI based method, comprising an additional step of integrating analysis and production of a product.

It is another object of the present invention to disclose the MRI based method, wherein least a part of said step of integrating analysis and production of a product complies with a NeSSI specification.

It is another object of the present invention to disclose the MRI based method, wherein at least a part of step of integrating analysis and production of a product complies with ANSI/ISA SP76.00.2002 miniature, modular mechanical standard specifications.

It is another object of the present invention to disclose the MRI based method, comprising an additional step of selecting a fluid within the body of a living subject as said flowing matter.

It is another object of the present invention to disclose the MRI based method, comprising an additional step of passing said fluid from the body of a living subject, through said envelope, and returning it to said living subject.

It is another object of the present invention to disclose the MRI based method, for imaging at least one first and at least one second image features; comprising an additional step of adapting said image processor to render said image by a Boolean method of correlating or combining said at least one first and at least one second image features.

It is another object of the present invention to disclose the MRI based method, comprising an additional step of selecting said Boolean operators of said Boolean method from the group consisting of OR, AND, NOT, EXCLUSIVE OR and any combination thereof.

It is another object of the present invention to disclose the MRI-based method as described hereinabove, comprising an additional step of selecting the fluid from a group consisting of potable water, sewage, irrigation water, sea water, river water, lake water, industrial effluent, farm effluent, effluent from human habitation, road runoff, blood, lymph, a beverage, cleaning fluid, and any combination thereof.

It is another object of the present invention to disclose an MRI-based system for providing high-contrast high-resolution images of a fluid comprising:
  a. the MRI device as defined hereinabove; and
  b. a fluid processing unit operation;
wherein the operation provided by said fluid processing unit operation is continuously online feedbacked by means of said MRI device.

It is another object of the present invention to disclose the MRI-based system, wherein said fluid processing unit operation is one of a group consisting of mixing, kneading, transporting, analyzing, reacting, cooking, freezing, controlling the temperature, controlling the pressure, emulsifying, de-emulsifying, gelation, de-gelation, liquidizing, polymerizing, de-polymerizing, controlling viscosity, controlling density, controlling particulate concentration, controlling particulate size, controlling particulate density, creating a suspension, clearing a suspension from the fluid, assessing contaminant levels, clearing contaminants, and any combination thereof.

It is another object of the present invention to disclose the MRI-based system, wherein said feedbacking comprises one of a group consisting of altering temperature, altering pressure, altering volume, altering mixing speed, altering mixing time, altering flow rate, altering composition of at least one component of the fluid, altering particulate size, altering particulate density, altering levels of electromagnetic radiation, altering wavelengths of electromagnetic radiation, altering degree of filtration, altering method of filtration, adding filters, removing filters, changing filters, starting at least some portion of the fluid processing unit operation, stopping at least some portion of the fluid processing unit operation, and any combination thereof.

It is another object of the present invention to disclose an MRI based method for integrating analysis and production of a product, at least one step of said production comprising a fluid processing, comprising:
  a. providing the MRI device as defined hereinabove;
  b. providing a fluid processing unit operation;
  c. operating said fluid processing unit operation;
  d. continuously generating said first at least one images, said second at least one images and said third superimposed at least one images, such that a high-contrast, high resolution real-time continuous image of said fluid is obtained
  e. analyzing said images of fluid operated on by said fluid processing unit operation generated by said MRI device, whereby a high-contrast, high resolution real-time continuous image of said fluid is obtained; and
  f. feedbacking the results of said analysis to said fluid processing unit
wherein the operation provided by said fluid processing unit operation is continuously online feedbacked by means of said MRI device.

It is another object of the present invention to disclose the MRI-based method, additionally comprising a step of selecting said fluid processing unit operation from a group consisting of mixing, kneading, transporting, analyzing, reacting, cooking, freezing, controlling the temperature, controlling the pressure, emulsifying, de-emulsifying, gelation, de-gelation, liquidizing, polymerizing, de-polymerizing, controlling viscosity, controlling density, controlling particulate concentration, controlling particulate size, controlling particulate density, creating a suspension, clearing a suspension from the fluid, assessing contaminant levels, clearing contaminants, and any combination thereof.

It is another object of the present invention to disclose the MRI-based method, additionally comprising a step of selecting said feedbacking from of a group consisting of altering temperature, altering pressure, altering volume, altering mixing speed, altering mixing time, altering flow rate, altering composition of at least one component of the fluid, altering particulate size, altering particulate density, altering levels of electromagnetic radiation, altering wavelengths of electromagnetic radiation, altering degree of filtration, altering method of filtration, adding filters, removing filters, changing filters, starting at least some portion of the fluid processing unit operation, stopping at least some portion of the fluid processing unit operation, and any combination thereof.

It is another object of the present invention to disclose an MRI-based system for screening for the presence of hazardous biological or chemical agent residues carried by an individual, comprising
  a. the MRI device as described hereinabove, said MRI device comprising an envelope for least partially confining a fluid;
  b. a fluid inlet in physical connection with said envelope;
  c. a fluid streamer for streaming a fluid over an individual passing through said fluid stream;
  d. a separator for separating out particles carried downstream by said fluid stream; and
  e. a particle collector for collecting said particles to provide a continuous fluid facilitated flow within said inlet to said envelope
whereby a high-contrast, high resolution real-time continuous image of said fluid is obtained and the presence of said hazardous biological or chemical agent residues is indicated.

It is another object of the present invention to disclose the MRI-based system, wherein the type of hazardous biological or chemical agent residues carried by said individual is indicated.

It is another object of the present invention to disclose the MRI-based system, wherein said fluid stream is an air curtain.

It is another object of the present invention to disclose the MRI-based system, wherein said separating is facilitated by a cyclone or filter or both.

It is another object of the present invention to disclose the MRI-based system, wherein said collecting of said particles is facilitated by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose an MRI-based method for screening for the presence of hazardous biological or chemical agent residues carried by an individual, comprising
  a. providing the MRI device as defined hereinabove, said MRI device comprising an envelope for least partially confining a fluid;
  b. providing said MRI with a fluid inlet in physical connection with said envelope;
  c. providing a fluid stream for said individual to pass through;
  d. streaming fluid over said individual passing through said fluid stream;
  e. separating out particles carried downstream by said fluid stream;
  f. collecting said particles by a particle collecting means to provide a continuous fluid facilitated flow within said inlet to said envelope; and
  g. continuously generating first at least one images, second at least one images and third superimposed at least one images, such that a high-contrast, high resolution real-time continuous image of said fluid is obtained
whereby the presence of said hazardous biological or chemical agent residues is indicated.

It is another object of the present invention to disclose the MRI-based method, comprising an additional step of indicating the type of hazardous biological or chemical agent residues carried by said individual.

It is another object of the present invention to disclose the MRI-based method, comprising an additional step of selecting said fluid stream to be an air curtain.

It is another object of the present invention to disclose the MRI-based method, comprising an additional step of facilitating said step of separating by means of a cyclone or filter or both.

It is another object of the present invention to disclose the MRI-based method, comprising an additional step of facilitating said step of collecting said particles by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose an MRI-based system for rapidly screening for the presence of hazardous biological or chemical residue in a flowing main fluid, comprising:
  a. the MRI device described hereinabove, said MRI device comprising an envelope for least partially confining a fluid;
  b. a main fluid;
  c. a purging device to separate at least one analyzable-size sample of fluid from said main fluid, said separator fluidly connected to said envelope;
  d. Functionalized Paramagnetic Particles (FPP) with a paramagnetic core and a moiety configured to interact with said biological or chemical agent residues;
  e. means for mixing said FPP with said at least one analyzable-size sample of fluid; and
  f. a facilitator to facilitate flow of said fluid mixed with said FPP through said MRI device;
whereby a high-contrast, high-resolution real-time continuous image of said at least one analyzable-size sample of said fluid is obtained, and further whereby the presence of said hazardous biological or chemical agent residues in said main fluid is indicated.

It is another object of the present invention to disclose the MRI-based system, wherein said step of separating is facilitated by means of a cyclone or filter or both.

It is another object of the present invention to disclose the MRI-based system, wherein said step of collecting said particles is facilitated by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose the MRI-based system, wherein the type of hazardous biological or chemical agent residues in said main fluid is indicated.

It is another object of the present invention to disclose the MRI-based system, wherein the fluid is one of a group consisting of potable water, sewage, irrigation water, sea water, river water, lake water, industrial effluent, farm effluent, effluent from human habitation, road runoff, blood, lymph, a beverage, cleaning fluid, and any combination thereof.

It is another object of the present invention to disclose an MRI-based method for rapidly screening for the presence of hazardous biological or chemical residue in a flowing main fluid, comprising
  a. providing the MRI device as defined above;
  b. purging said main fluid to an analyzable-size sample;
  c. facilitatedly flowing said purged fluid through said MRI;
  d. providing Functionalized Paramagnetic Particles (FPP) with a paramagnetic core and a moiety configured to interact with said biological or chemical agent residues;
  e. introducing said FPP within said purged fluid, f. if said hazardous biological or chemical residue is present in said purged fluid, then interacting said FPP with said biological or chemical agent residues;
a. generating multiple time resolved one or more first images at high resolution of at least a portion of said purged fluid;
b. generating multiple time resolved one or more second images at high contrast of at least portion of same said purged fluid;
g. superimposing at least one image of said first images with at least one image of said second images whereby a high-contrast, high resolution real-time continuous image of said purged fluid is obtained;
h. measuring a change in a nuclear relaxation property of said purged fluid caused by said interaction between said FPP and said biological or chemical agent residues in the applied magnetic field, as indicated by said high-contrast, high resolution real-time continuous image of said purged fluid; and
i. correlating said change to the presence of said biological or chemical agent residues in said purged fluid, whereby the presence of said hazardous biological or chemical agent residues in said main fluid is indicated.

It is another object of the present invention to disclose the MRI-based method, additionally comprising a step of facilitating said step of separating by means of a cyclone or filter or both.

It is another object of the present invention to disclose the MRI-based method, wherein said step of collecting said particles is facilitated by a particle collecting means selected from a group comprising activated carbon, a filter including air filter, water filter, paper filter, HEPA filter, microfilter, water filter, water curtain, other conventional filter, other collection device, and any combination thereof.

It is another object of the present invention to disclose the MRI-based method, additionally comprising a step of indicating the type of hazardous biological or chemical agent residues in said main fluid.

It is another object of the present invention to disclose the MRI-based method, additionally comprising a step of selecting the fluid to be one of a group consisting of potable water, sewage, irrigation water, sea water, river water, lake water, industrial effluent, farm effluent, effluent from human habitation, road runoff, blood, lymph, a beverage, cleaning fluid, and any combination thereof.

The invention claimed is:

1. An MRI based method for providing high contrast high resolution images of a fluid, comprising:
    a. providing an envelope for least partially confining said fluid;
    b. providing a plurality of magnets located at least partially around said envelope, said assembly comprising
        i. a least one first magnet configured to provide a high magnetic field for generating multiple time-resolved one or more first images at high resolution of at least a portion of said fluid; and
        ii. a least one second magnet configured to provide a low magnetic field for generating multiple time-resolved one or more second images at high contrast of at least portion of same said fluid; wherein at least one image of said first images and at least one image of said second images being generated in a time no greater than approximately the time between two first images;
    c. providing a CPU to process said images comprising a computer readable medium containing instructions for generating at least one third image superimposing at least one image of said first images with at least one image of said second images;
    d. generating multiple time resolved one or more first images at high resolution of at least a portion of said fluid;
    e. generating multiple time resolved one or more second images at high contrast of at least portion of same said fluid; and
    f. superimposing at least one image of said first images with at least one image of said second images
    whereby a high-contrast, high resolution real-time continuous image of said fluid is obtained.

2. The MRI based method of claim 1, comprising an additional step of selecting said at least one first magnet to be of 2 Tesla and lower.

3. The MRI based method of claim 1, comprising an additional step of selecting said at least one first magnet to be of 2 Tesla and higher.

4. The MRI based method of claim 1, comprising an additional step of selecting said at least one first magnet from a group consisting of permanent magnets, electromagnets, superconducting magnets, and any combination thereof.

5. The MRI based method of claim 1, comprising an additional step of selecting said at least one second magnet to be of 2 Tesla and lower.

6. The MRI based method of claim 1, comprising an additional step of selecting said at least one second magnet to be of 2 Tesla and higher.

7. The MRI based method of claim 1, comprising an additional step of selecting said at least one second magnet from a group consisting of permanent magnets, electromagnets, superconducting magnets, and any combination thereof.

8. The MRI based method of claim 1, wherein a single RF coil is used for generating said one or more first images and said one or more second images.

9. The MRI based method of claim 1, comprising an additional step of having the angle between a perpendicular to the direction of flow and said high magnetic field not the same as the angle between said perpendicular to the direction of flow and said low magnetic field.

10. The MRI based method of claim 1, comprising an additional step of selecting an integrated MRI device comprising both said high magnetic field magnets and said low magnetic field magnets.

11. The MRI based method of claim 1, comprising an additional step of selecting said MRI device comprising two MRI devices, one providing the high magnetic field magnets and one providing the low magnetic field magnets.

12. The MRI based method of claim 1, comprising an additional step of selecting a duty cycle for said high magnetic field magnets greater than approximately 50% and a duty cycle for said low magnetic fields magnets less than approximately 50%.

13. The MRI based method of claim 1, comprising an additional step of selecting said envelope from a group consisting of a pipe, a duct, a tunnel, a conduit, a tube, a conveyor, a channel, a passage, and any combination thereof.

14. The MRI based method of claim 1, comprising an additional step of forming said envelope as an integral part of at least one MRI device.

15. The MRI based method of claim 1, comprising an additional step of selecting said fluid from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

16. The MRI based method of claim 1, comprising an additional step of providing said fluid within the fluid process stream in a production process.

17. The MRI based method of claim 16, comprising an additional step of selecting said production process in an industrial area, said industrial area a member of a group consisting of the pharmaceuticals, food production, beverage production, chemical refining, chemical processing, medical products, biological products, metal casting, metal refining, desalination, fluid purification, and sewage processing.

18. The MRI based method of claim 17, comprising an additional step of selecting water as the fluid purified in said fluid purification.

19. The MRI based method of claim 16, further comprising integrating said method into a production system.

20. The MRI based method of claim 1, comprising an additional step of providing said fluid within a bypass stream from a production line.

21. The MRI based method of claim 1, comprising an additional step of providing said fluid in the fluid process stream within a batch process.

22. The MRI based method of claim 1, comprising an additional step of providing said fluid within an engine or combustion chamber.

23. The MRI based method of claim 1, comprising an additional step of providing said fluid as the effluent from said engine or combustion chamber.

24. The MRI based method of claim 1, comprising an additional step of providing said fluid as some fraction of the effluent from said engine or combustion chamber.

25. The MRI based method of claim 1, comprising an additional step of selecting a fluid used in fertility treatments.

26. The MRI based method of claim 1, comprising an additional step of selecting a fluid used for artificial insemination.

27. The MRI based method of claim 1, comprising an additional step of selecting a fluid containing liposomes.

28. The MRI based method of claim 1, comprising an additional step of selecting a fluid which is part of an air curtain.

29. The MRI based method of claim 1, comprising an additional step of selecting a fluid which is a polymeric melt.

30. The MRI based method of claim 29, comprising an additional step of selecting said polymeric melt from a group consisting of rubbers, polyesters, polyamides, polypropylenes, polyethylenes, polyurethanes, and any combination thereof.

31. The MRI based method of claim 1, comprising an additional step of selecting a fluid within the body of a living subject as said flowing matter.

32. The MRI based method of claim 31, comprising an additional step of passing said fluid from the body of a living subject, through said envelope, and returning it to said living subject.

33. The MRI based method of claim 1, wherein said step of superimposing comprises using Boolean operators for correlating or combining said at least one image of said first images and said at least one image of said second images.

34. The MRI based method of claim 33, wherein said Boolean operators are selected from the group consisting of OR, AND, NOT, EXCLUSIVE OR and any combination thereof.

35. The MRI-based method of claim 1, comprising an additional step of selecting the fluid from a group consisting of potable water, sewage, irrigation water, sea water, river water, lake water, industrial effluent, farm effluent, effluent from human habitation, road runoff, blood, lymph, a beverage, cleaning fluid, and any combination thereof.

* * * * *